(12) United States Patent
Wu et al.

(10) Patent No.: US 9,422,214 B2
(45) Date of Patent: Aug. 23, 2016

(54) METHOD FOR SCALE EXTRACTION QUEBRACHITOL FROM NATURAL RUBBER INDUSTRY WASTE WATER

(71) Applicant: YUNNAN INSTITUTE OF TROPICAL CROPS, Jinghong, Yunnan Province (CN)

(72) Inventors: Ying Wu, Jinghong (CN); Shikuan Jiang, Jinghong (CN); Gouhua Li, Jinghong (CN); Guimei Zhang, Jinghong (CN); Jianyun Zou, Jinghong (CN); Rong Xu, Jinghong (CN)

(73) Assignee: YUNNAN INSTITUTE OF TROPICAL CROPS, Jinghong (CN)

( * ) Notice: Subject to any disclaimer, the term of this patent is extended or adjusted under 35 U.S.C. 154(b) by 0 days.

(21) Appl. No.: 14/403,230

(22) PCT Filed: May 17, 2013

(86) PCT No.: PCT/CN2013/075778
§ 371 (c)(1),
(2) Date: Nov. 24, 2014

(87) PCT Pub. No.: WO2014/107942
PCT Pub. Date: Jul. 17, 2014

(65) Prior Publication Data
US 2015/0105591 A1    Apr. 16, 2015

(30) Foreign Application Priority Data

Jan. 9, 2013   (CN) .......................... 2013 1 0007459

(51) Int. Cl.
C07C 41/40    (2006.01)
C07C 43/196   (2006.01)
C07C 41/36    (2006.01)

(52) U.S. Cl.
CPC ............... *C07C 41/40* (2013.01); *C07C 41/36* (2013.01); *C07C 43/196* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 1,758,616 A | 5/1930 | McGavack et al. | |
| 2,378,141 A | 6/1945 | Hart | |
| 5,041,689 A | 8/1991 | Udagawa et al. | |
| 2013/0203688 A1* | 8/2013 | Barbeau ................ | A23L 1/3002 514/25 |

FOREIGN PATENT DOCUMENTS

| | | | |
|---|---|---|---|
| CN | 102516041 | * | 6/2012 |
| CN | 102516041 A | | 6/2012 |
| CN | 102557892 A | | 7/2012 |
| CN | 102731270 A | | 10/2012 |
| CN | 103058834 A | | 4/2013 |
| GB | 572128 A | | 9/1945 |

OTHER PUBLICATIONS

AMNP, Attanayake et al. (2001) "*Isolation and Publication of Quebrachitol from Rubber Factor Effluents*," Preceedings of the Seventh Annual Forestry and Environment Symposium, p. 57.

Deng, Y. & Deng, D. (2000) "*Study on Extraction of Quebrachitol from Natural Rubber*," Natural Product Research and Development 12(6):61-65.

Deng, Y. & Ao, N. (2005) "*Study on the Contents of Quebrachitol in Natural Latex with Different Latex Preservatives Treating*," Journal of Yunnan Agricultural University 20(3):326-330.

\* cited by examiner

*Primary Examiner* — Rosalynd Keys
(74) *Attorney, Agent, or Firm* — Pearl Cohen Zedek Latzer Baratz LLP

(57) ABSTRACT

Provided is a method for scale extraction of quebrachitol from natural rubber industry waste water, the method comprising the following steps: coarsely filtering the natural rubber industry waste water to obtain a waste water clear liquor A; filtering the waste water clear liquor A with an ultrafiltration membrane to obtain a filtrate B; concentrating the filtrate B with a nanofiltration membrane or a reverse osmosis membrane to obtain a concentrated solution C; decolorizing and then evaporating and concentrating the concentrated solution C, to obtain a pasty concentrated solution D; cooling the pasty concentrated solution D for crystallization, and collecting the crystals to obtain a coarse product E; and purifying the coarse product E to obtain a pure quebrachitol. The technology process of the method is simple and low cost, scale production can be achieved, and the purity of the obtained product can be up to 99%.

19 Claims, 3 Drawing Sheets

METHOD FOR SCALE EXTRACTION QUEBRACHITOL FROM NATURAL RUBBER INDUSTRY WASTE WATER

CROSS REFERENCE TO RELATED APPLICATIONS AND CLAIM TO PRIORITY

This Application is a national application of International Application No. PCT/CN2013/075778 (filed on May 17, 2013), which claims priority to Chinese Patent Application No. 201310007459.X (filed on Jan. 9, 2013), which applications are herein incorporated by reference in their entireties.

TECHNICAL FIELD

The present application relates to the extraction of Quebrachitol, and more specifically, to a method for scale extraction of Quebrachitol from natural rubber industry waste water.

BACKGROUND ART

Quebrachitol (L-Quebrachitol), i.e. L-inositol methyl ether, whose English chemical name is 2-O-methyl-L-(−)-chiro-inositol, is a natural optically active inositol widely presented in plants. It has been proved that quebrachitol plays an important role of "delivering intra-cell information" and "controlling growth process of cells" in living organism metabolism. As a chiral structure unit, quebrachitol can be easily converted into various inositol derivatives widely used in biology and medicine fields. Therefore, quebrachitol has gained much attention from biochemistry, pharmacology and medicine experts.

Quebrachitol was firstly discovered in quebracho of South America, and later, such component was also discovered in plants such as Maple, *Allophylus edulis, Mitrephora vulpine*, Hemp, *Eleagnus formosana* and so on. Although many plants contain quebrachitol, its content is generally relatively low. *Hevea brasiliensis* is a plant rich in quebrachitol and the content of quebrachitol in it occupies about 0.2%-1.2% by weight of the rubber latex, and thus it is currently a quebrachitol source with the highest industrialization value.

Natural rubbers are widely planted in tropical and subtropical regions. After development of several decades, a well mature industry system has been formed, and its industrial production has also become stable. The industrial production of natural rubber industry can only be further increased by making great efforts in developing comprehensive utilization of natural rubber by-products. Undoubtedly, it is an important approach to extract quebrachitol from natural rubber industry waste water. Natural rubber factories produce a large amount of industrial waste water each year, and serum, when discharged as waste water, does not only pollute environment, but also wastes resources. Scientists make continuous study on extraction of quebrachitol, and file related patents. However, the extraction scale is always limited to laboratory stage, and it is hard to perform scale production. Moreover, high cost also restricts the search and application of quebrachitol. Therefore, there is a need for a technology process for industrialized extraction of quebrachitol at a low cost.

SUMMARY OF THE INVENTION

The purpose of the present application is to provide a method for scale extraction of quebrachitol from natural rubber industry waste water.

Specifically, the present application provides a method for scale extraction of quebrachitol from natural rubber industry waste water, comprising the following steps:

coarsely filtering the natural rubber industry waste water to obtain a waste water clear liquor A;

filtering the waste water clear liquor A with an ultrafiltration membrane to obtain a filtrate B;

concentrating the filtrate B with a nanofiltration membrane or a reverse osmosis membrane to obtain a concentrated solution C;

decolorizing, and then evaporating and concentrating the concentrated solution C to obtain a pasty concentrated solution D;

cooling the pasty concentrated solution D for crystallization, collecting the crystals, to obtain a coarse product E; and purifying the coarse product E to obtain a pure quebrachitol.

Wherein, the natural rubber industrial waste water comprises all waste water containing serum generated in every stage of natural rubber processing.

In some embodiments, the coarse filtration may be implemented using a sieve, a filter bag, or a plate-and-frame filter press to remove solid impurities, remaining rubber and floccules. Moreover, the coarsely filtration in the present application may also be implemented in other manners known in the art.

In some embodiments, the decolouration is implemented by using activated carbon, bone charcoal or activated clay. Moreover, the decolouration in the present application may also be implemented using other decoloring agents known in the art.

In some embodiments, the purification may be implemented through recrystallization.

Wherein, the purification may also be implemented in other purification manners known in the art, for example, macroporous adsorption resin, silica gel column chromatography and the like.

In some embodiments, a solvent used for recrystallization may be water, a mixed solution of ethanol and water, and a mixed solution of acetic acid and water. Wherein, the ratio of ethanol to water in the mixed solution of ethanol and water is not limited, and the ratio of acetic acid to water in the mixed solution of acetic acid and water is also not limited. Meanwhile, in consideration of the costs, preferably, the solvent used for recrystallization is water, and more preferably, the solvent used for recrystallization is distilled water.

In some embodiments, recrystallization may be implemented for multiple times, preferably, for three times.

In some embodiments, the method further comprises a step of heating the natural rubber industry waste water before coarsely filtering, so as to remove part of remaining rubber and protein, and meanwhile facilitating implementation of membrane separation.

In some embodiments, the heating temperature is above 80, until the natural rubber industry waste water boils. Wherein, a duration of heating may be selected according to specific conditions, but it is generally keeping 3-5 minutes after the occurrence of flocculate of protein and remaining rubber.

In some embodiments, the method may further comprise a step of filtering the waste water clear liquor A with a microfiltration membrane before filtering with an ultrafiltration membrane. Wherein, the filtration of micro-filtration membrane is mainly for intercepting solid suspended particles, bacteria, macromolecule colloidal substances, etc.

In some embodiments, the pore diameter of the microfiltration membrane is 0.01 μm-10 μm.

In some embodiments, the ultrafiltration membrane is an ultrafiltration membrane with an interception molecular weight of 1000 Da-100 000 Da, and the nanofiltration membrane is a nanofiltration membrane with an interception molecular weight below 1000 Da.

After analysis, it has been found that the natural rubber industrial waste water is mainly composed of serum discharged after rubber processing, and further contains proteins, lipoids, water solubles, acetone solubles and inorganic salts, etc, in addition to a small amount of non-solidified rubbers. The ultrafiltration membrane is mainly for removing macromolecule substances such as proteins, lipoids, acetone solubles and the like. The nanofiltration membrane mainly plays the role of concentration, and meanwhile it can remove small molecules inorganic salts, pigments and the like. The reverse osmosis membrane only has the concentrating function.

In the present application, membrane separation technology is adopted for purifying and concentrating the natural rubber industrial waste water and the crystallization is adopted for extracting quebrachitol. Such method of the present application is a process technology for scale extracting quebrachitol at a low cost.

Compared with the prior art, the method of the present application has the following benefits:

(1) a large amount of waste water will be discharged during the production from the natural rubber processing factories, therefore, the raw materials are very rich and cheap;

(2) waste water processing pressure undertook by the rubber factories can be relieved, and meanwhile wastes becomes valuable, and the additional value of natural rubber industry is increased;

(3) the technology process is easy and low cost, scale production can be achieved, and the obtained product has a high purity.

PREFERRED EMBODIMENTS OF THE PRESENT INVENTION

Figure 1:
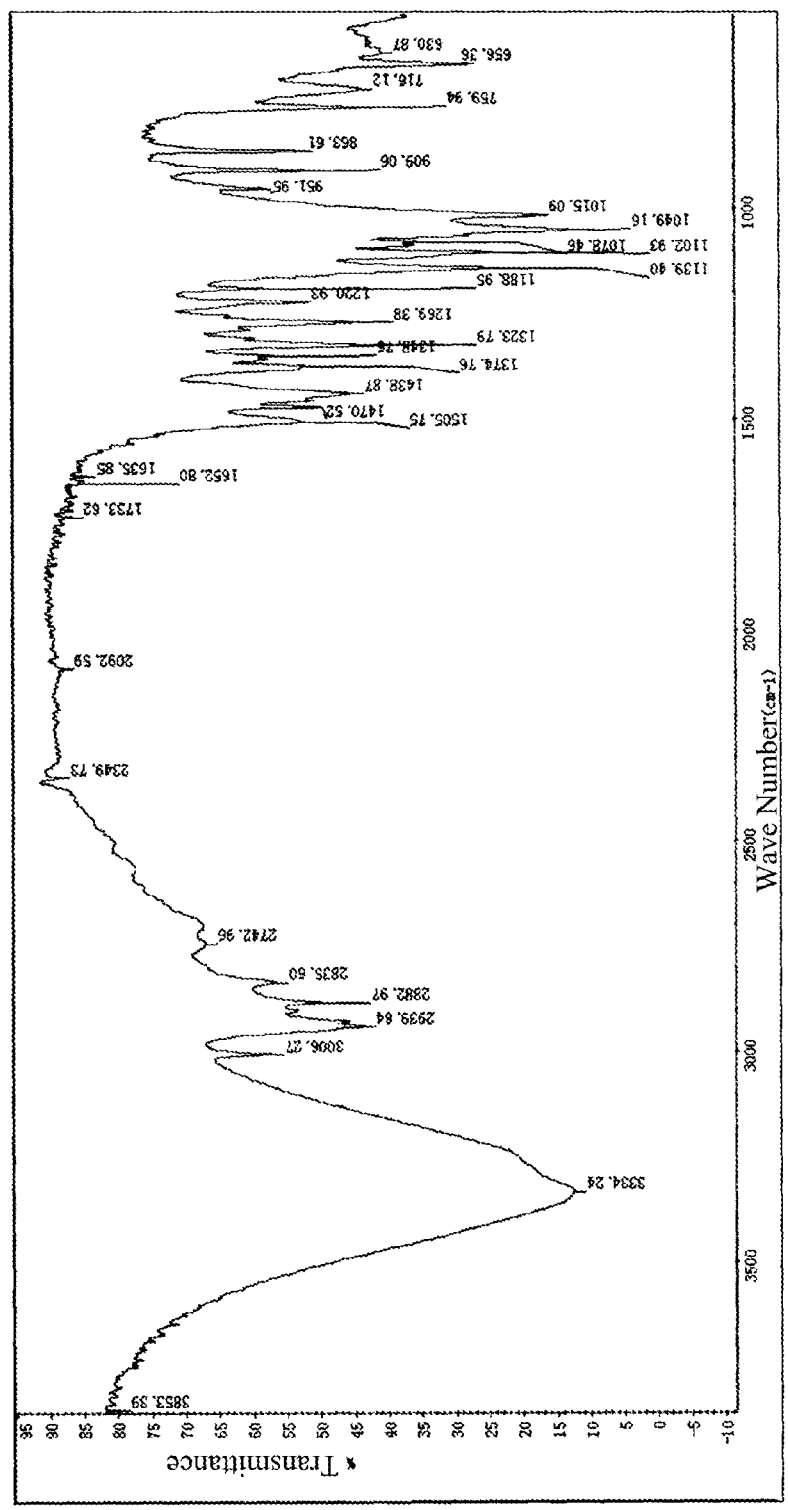
FIG. 1 is an infrared chromatogram of a standard product for comparison in Example 1.

The embodiments of the present application will be described in connection with examples. A person having ordinary skill in the art should appreciate that these specific examples are only embodiments selected for achieving the purpose of the present application, and are not intended to limit the technical solutions. Improvements made to the technical solutions of the present application according to the teaching of the present application in combination with the prior art are obvious and should all fall into the protection scope of the present application.

Wherein, the micro-filtration membrane, ultrafiltration membrane, nanofiltration membrane, and reverse osmosis membrane used in the following examples are purchased from General Electric (GE). Wherein, the model numbers of the micro-filtration membrane are EW1812C-34D (pore diameter: 0.04 μm), JX1812C-34D (pore diameter: 0.3 μm); the model numbers of the ultrafiltration membrane are GE1812C-34D (1000 Da), GH1812C-34D (2500 Da), PT1812C-34D (5000 Da); the model numbers of the nanofiltration membrane are DK1812C-34D (150-300 Da), DL1812C-34D (150-300 Da); the model number of the reverse osmosis membrane is SG1812C-34D. The natural rubber industrial waste water is from Natural Rubber Factory of Xishuangbanna of Yunnan.

Example 1

40 kg of natural rubber industrial waste water was heated to boil, and the heating was kept for 3 minutes after the occurrence of flocculate of proteins and remaining rubber. Solid impurities were removed by filtering with a sieve to obtain 39 kg of waste water clear liquor A. A micro-filtration membrane (pore diameter: 0.04 μm) was used to filter the waste water clear liquor A to remove macromolecule soluble matters such as proteins, obtaining 31 kg of a filtrate B. An ultrafiltration membrane (interception molecular weight: 5000 Da) was used to filter the filtrate B so as to further remove soluble impurities, obtaining 28.5 kg of a filtrate C'; an ultrafiltration membrane (interception molecular weight: 1000 Da) was further used to filter the filtrate C', obtaining 25 kg of a filtrate C. A nanofiltration membrane (interception molecular weight: 150-300 Da) was used to concentrate the filtrate C to obtain 3 kg of a concentrate D, into which 30 g (account for 1% of the weight of the concentrate) of activated carbon was added to perform decoloration, reduced pressure distillation was performed after suction filtration, giving 480 g of a pasty concentrate E, which was cooled to the room temperature and then placed in a 4 refrigerator. Crystals were collected after 12 hours, and the crystals were subjected to recrystallization with 75% (mass ratio) ethanol aqueous solution for three times, obtaining 42 g of colorless quebrachitol crystal, and the purity of the colorless quebrachitol crystal was 99.20% as measured by a highly-efficient liquid phase chromatography external standard method.

Figure 3:
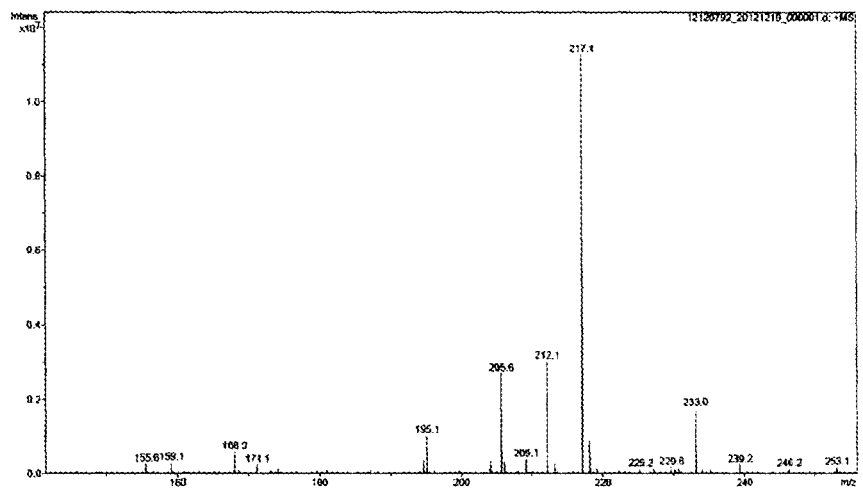
FIG. 3 is a mass spectrogram of a standard product for comparison in Example 1.
Figure 4:
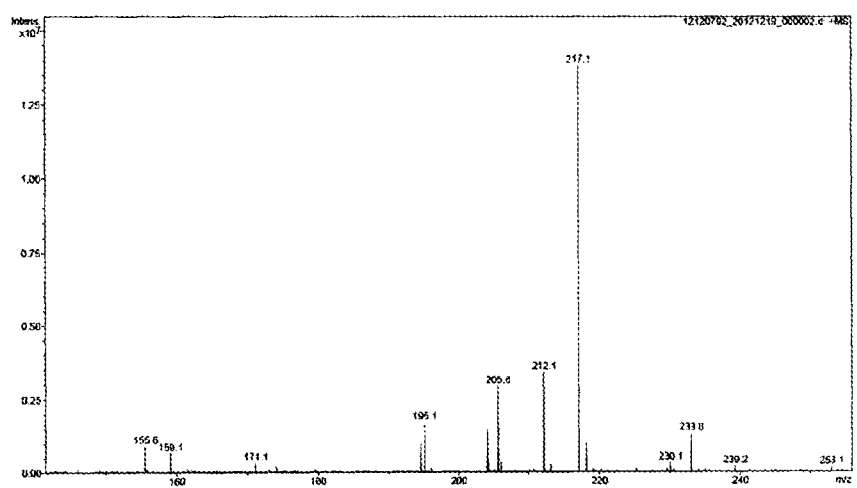
FIG. 4 is mass spectrogram of quebrachitol obtained from purification in Example 1.

Wherein, the mass spectrum analysis result of the obtained colorless quebrachitol crystal is: 195(M+H), 217(M+Na), which was consistent with the standard product (195(M+H), 217(M+Na)). Please see FIG. 3 and FIG. 4 for details.

The infrared chromatography information of the obtained colorless quebrachitol crystal is as below: 3334.78 cm$^{-1}$ (br, s, vOH hydroxy stretching vibration peak), 2939.69 cm$^{-1}$ (s, vas C—H methylene asymmetric stretching vibration), 2882.94 cm$^{-1}$ (s, vs C—H methylene symmetric stretching vibration)), 1470.82 cm$^{-1}$ (s, δ C—H methylene bending vibration), 1374.99 cm$^{-1}$ (s, δs C—H methyl bending vibration), 1139.32 cm$^{-1}$, 1102.99 cm$^{-1}$ (s, vas C—O—C ether bond stretching vibration)

The infrared chromatography information of the standard product is as below:

3334.24 cm$^{-1}$ (br, s, vOH hydroxy stretching vibration peak), 2939.64 cm$^{-1}$ (s, vas C—H methylene asymmetric stretching vibration), 2882.97 cm$^{-1}$ (s, vs C—H methylene symmetric stretching vibration), 1470.52 cm$^{-1}$ (s, δC—H methylene bending vibration), 1374.76 cm$^{-1}$ (s, δs C—H methyl bending vibration), 1139.40 cm$^{-1}$, 1102.93 cm$^{-1}$ (s, vas C—O—C ether bond stretching vibration)

Figure 2:
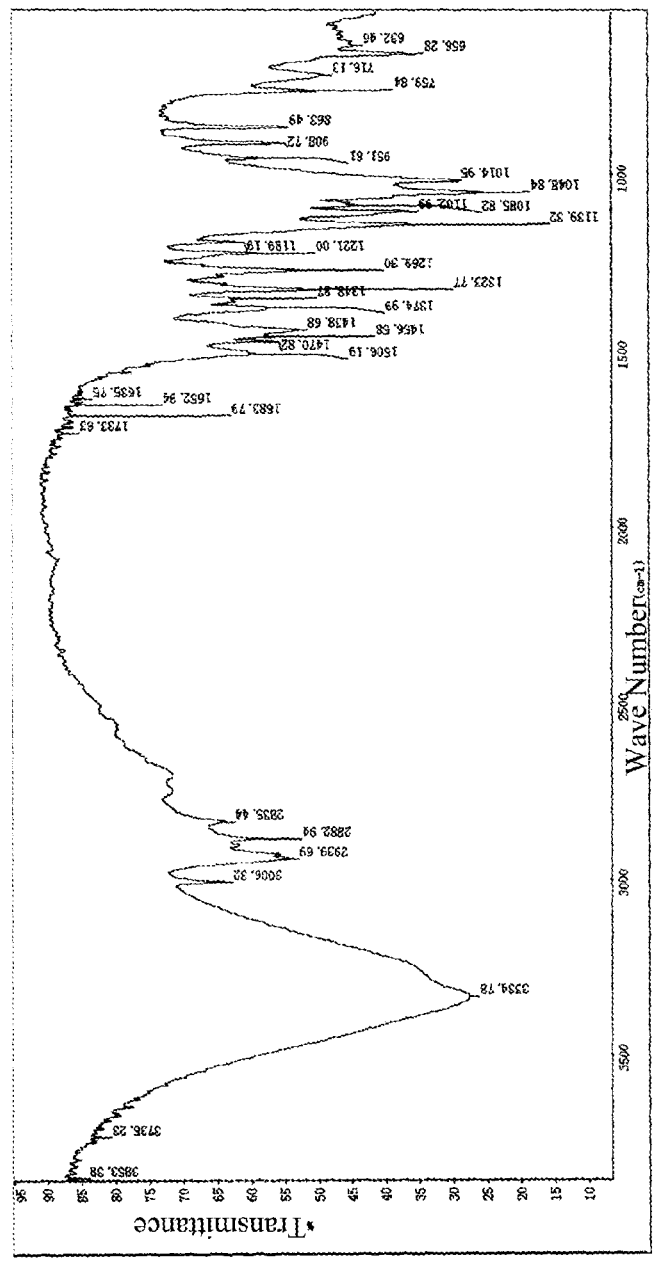
FIG. 2 is an infrared chromatogram of quebrachitol obtained from purification in Example 1.

Therefore, the infrared chromatography information of the obtained colorless quebrachitol crystal is consistent with the infrared chromatography information of the standard product. Please see FIG. 2 and FIG. 3 for more details.

Example 2

40 kg of natural rubber industrial waste water was heated to 85, and the heating was kept for 5 minutes after the occurrence of flocculate of proteins and remaining rubber, solid impurities were removed with a filter bag to obtain 34 kg of waste water clear liquor A. A micro-filtration membrane (pore diameter: 0.04 μm) was used to filter the waste water clear liquor A to remove macromolecule soluble matters such as proteins, obtaining 31 kg of a filtrate B. An ultrafiltration membrane (interception molecular weight: 2500 Da) was used to filter the filtrate B so as to further remove soluble impurities, obtaining 27 kg of a filtrate C; a reverse osmosis membrane was used to concentrate the filtrate C, obtaining 4 kg of a concentrate D, into which 60 g of bone charcoal was added, reduced pressure distillation was performed after suction filtration, giving 520 g of a pasty concentrate E, which was cooled to the room temperature, crystals were collected after 12 hours, and the crystals were subjected to recrystallization with distilled water for three times, obtaining 45 g of colorless quebrachitol crystal, the purity of the colorless quebrachitol crystal was 98.92% as measured by a highly-efficient liquid phase chromatography external standard method.

The related mass spectrum and infrared chromatography information of the obtained colorless quebrachitol crystal is same as those in Example 1.

Example 3

40 kg of natural rubber industrial waste water was filtered with a plate-and-frame filter press to remove solid impurities, obtaining 39.5 kg of waste water clear liquor A. A micro-filtration membrane (pore diameter: 0.3 μm) was used to filter the waste water clear liquor A, obtaining 32 kg of a filtrate B. An ultrafiltration membrane (interception molecular weight: 2500 Da) was used to filter the filtrate so as to further remove soluble impurities, obtaining 22 kg of a filtrate C; a nanofiltration membrane (interception molecular weight: 150-300 Da) was used to concentrate the filtrate C, obtaining 2.8 kg of a concentrate D, into which 14 g of activated clay was added, reduced pressure distillation was performed after suction filtration, giving 350 g of a pasty concentrate E, which was cooled to the room temperature, crystals were collected after 12 hours, and the crystal were subjected to recrystallization with a pure acetic acid solution for three times, obtaining 33 g of colorless quebrachitol crystal, the purity of colorless quebrachitol crystal was 99.05 as measured by a highly-efficient liquid phase chromatography external standard method.

The related mass spectrum and infrared chromatography information of the obtained colorless L-Quebrachitol crystal is same as those in Example 1.

The present application includes, but not limited to, the above examples. Any equivalent substitutions or local improvements made within the spirit and principle of the present application shall be deemed to fall within the protection scope of the present application.

INDUSTRIAL APPLICABILITY

In the present application, membrane separation technology is adopted for edulcoration and concentration of the natural rubber industrial waste water and the crystallization is adopted for extracting quebrachitol. Such method of the present application is a technology process for scale extracting quebrachitol at a low cost.

What is claimed is:

1. A method for scale extraction of quebrachitol from natural rubber industry waste water, comprising the following steps:

coarsely filtering the natural rubber industry waste water to obtain a waste water clear liquor A;

filtering the waste water clear liquor A with an ultrafiltration membrane to obtain a filtrate B;

concentrating the filtrate B with a nanofiltration membrane or a reverse osmosis membrane to obtain a concentrated solution C;

decolorizing, and then evaporating and concentrating the concentrated solution C to obtain a pasty concentrated solution D;

cooling the pasty concentrated solution D for crystallization, collecting the crystals, to obtain a coarse product E; and purifying the coarse product E to obtain a pure quebrachitol.

2. The method according to claim 1, wherein the coarse filtration is implemented using a sieve, a filter bag, or a plate-and-frame filter press.

3. The method according to claim 1, wherein the decoloration is implemented by using activated carbon, bone charcoal or activated clay.

4. The method according to claim 1, wherein the purification is implemented through recrystallization.

5. The method according to claim 4, wherein a solvent used for the recrystallization is water, a mixed solution of ethanol and water, or a mixed solution of acetic acid and water.

6. The method according to claim 4, wherein, the recrystallization is performed for three times.

7. The method according to claim 1, further comprising a step of heating the natural rubber industry waste water before the coarsely filtering.

8. The method according to claim 1, further comprising a step of filtering the waste water clear liquor A with a micro-filtration membrane before filtering with an ultrafiltration membrane.

9. The method according to claim 8, wherein a pore diameter of the micro-filtration membrane is 0.01 μm-10 μm.

10. The method according to claim 1, wherein, the ultra-filtration membrane is an ultrafiltration membrane with an interception molecular weight of 1000 Da-100 000 Da.

11. The method according to claim 1, wherein the nanofiltration membrane is a nanofiltration membrane with an interception molecular weight below 1000 Da.

12. The method according to claim 5, wherein the recrystallization is performed for three times.

13. The method according to claim 5, wherein the solvent used for the recrystallization is water.

14. The method according to claim 13, wherein the solvent used for the recrystallization is distilled water.

15. The method according to claim 7, wherein the heating is maintained 3-5 minutes after the occurrence of flocculate of protein and remaining rubber.

16. The method according to claim 8, wherein the micro-filtration membrane is used for intercepting solid suspended particles, bacteria, and macromolecule colloidal substances.

17. The method according to claim 1, wherein the ultrafiltration membrane is used for removing proteins, lipoids, and acetone solubles.

18. The method according to claim 1, wherein the nanofiltration membrane is used for concentration, and removing small molecules inorganic salts and pigments.

19. The method according to claim 1, wherein the reverse osmosis membrane is used for concentration.

* * * * *